US006733637B1

(12) United States Patent
Burton et al.

(10) Patent No.: US 6,733,637 B1
(45) Date of Patent: May 11, 2004

(54) PROCESS FOR PRODUCING ULTRA-HIGH PURITY ISOPROPANOL

(75) Inventors: Paul E. Burton, Baton Rouge, LA (US); Dennis J. Davoren, Baton Rouge, LA (US); Timothy P. Dean, Baton Rouge, LA (US); John P. Motlow, Baton Rouge, LA (US); Charles M. Yarbrough, Baton Rouge, LA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/587,103

(22) Filed: Jun. 2, 2000

(51) Int. Cl.[7] .................. B01D 3/00; B01D 15/00; C07C 27/28
(52) U.S. Cl. .................. 203/14; 203/18; 203/99; 203/DIG. 19; 210/640; 210/651; 210/660; 210/664; 568/913; 568/916
(58) Field of Search .................. 203/14, 18, 99, 203/DIG. 19, 100, 57; 210/638, 640, 651, 653, 660, 664, 500.27, 634; 568/913; 159/DIG. 27, DIG. 28

(56) References Cited

U.S. PATENT DOCUMENTS

| 4,399,000 A | | 8/1983 | Tedder | |
|---|---|---|---|---|
| 4,762,616 A | * | 8/1988 | Litzen et al. | 210/634 |
| 4,788,043 A | * | 11/1988 | Kagiyama et al. | 210/500.27 |
| 4,879,041 A | * | 11/1989 | Kurokawa et al. | 210/640 |
| 5,494,556 A | | 2/1996 | Mita et al. | |
| 5,571,387 A | | 11/1996 | Marker et al. | |
| 5,585,527 A | | 12/1996 | Marker | |
| 5,868,906 A | | 2/1999 | Adams et al. | |
| 5,897,750 A | | 4/1999 | Berg | |

* cited by examiner

Primary Examiner—Virginia Manoharan

(57) ABSTRACT

A process for producing high purity isopropyl alcohol. In one embodiment, the process includes the steps of: (a) feeding a feed stream comprising at least about 99.9 wt. % isopropyl alcohol into a separation column; (b) separating the isopropyl alcohol into an overhead stream taken overhead from the separation column and a bottoms stream taken as bottoms from the separation column; and (c) removing the high purity isopropyl alcohol at a point: (i) below where the feed stream enters the separation column but above the bottoms stream, or (ii) above where the feed stream enters the separation column but below the overhead stream. The high purity isopropyl alcohol has a metals content of less than about 1 ppb and a water content of less than about 100 ppm. Optionally, the process includes the step of passing the high purity isopropyl alcohol through an ion exchange resin after removing the high purity isopropyl alcohol from the separation column, thereby forming an ultra-high purity isopropyl alcohol that contains less than 100 ppt of any metal impurity.

10 Claims, 6 Drawing Sheets

PROCESS FOR PRODUCING ULTRA-HIGH PURITY ISOPROPANOL

FIELD OF THE INVENTION

The present invention relates to a process for producing ultra-high purity isopropyl alcohol. More particularly, the present invention relates to a process for producing ultra-high purity isopropyl alcohol that has less than 100 parts per trillion of metal impurities and less than 100 parts per million water.

BACKGROUND OF THE INVENTION

Semiconductor manufacturing operations require that wafer surfaces be as clean as possible. At times this is difficult, especially when the wafer or chip is rinsed with an aqueous solution and subsequently dried. The process of drying often leads to the formation of spots, leaving unwanted residue on the surface. This can be a nuisance that leads to defects in the manufacturing process.

One solution to this residue problem is to immediately follow the aqueous rinse with a rinsing solution containing isopropyl alcohol. The isopropyl alcohol quickly evaporates, leaving no residue behind.

In order for this method to be effective, the isopropyl alcohol must be extremely pure. This new requirement has created a need to develop processes that purify isopropyl alcohol to unusually high purity levels, typically where contaminants and water are measured in parts per million and/or lower.

Several patents describe processes used to produce a high purity isopropyl alcohol product. However, none of these patents disclose the processes described and claimed by the present invention:

U.S. Pat. No. 5,868,906 issued to Adams et al. on Feb. 9, 1999 teaches a method for dehydrating and purifying impure isopropyl alcohol by removing substantially all the water and any organic impurities with boiling points less than isopropyl alcohol from an isopropyl alcohol solution containing less than 2000 parts per million water in a first distillation column. The overhead product contains organic substances with boiling points less than isopropyl alcohol and a binary isopropyl alcohol/water azeotrope. The overhead product from the first distillation column feeds a second distillation column, where a low boiling overhead product is taken and filtered to a desired specification.

U.S. Pat. No. 2,604,440 issued to Brooks on Jul. 22, 1952 discloses a process where isopropyl alcohol is purified by removing water from an isopropyl alcohol-water binary azeotrope in the presence of sulfuric acid.

U.S. Pat. No. 4,399,000 issued to Tedder on Aug. 16, 1983, teaches a process for producing alcohol substantially free of water. The process comprises the steps of extracting an aqueous alcohol solution with an organic solvent system containing an extractant for the alcohol, thereby forming an organic solvent-alcohol phase and an aqueous phase, and vacuum distilling the organic solvent-alcohol phase thereby obtaining the product alcohol substantially free of water.

U.S. Pat. No. 5,585,527 issued to Marker on Dec. 17, 1996 and U.S. Pat. No. 5,571,387 issued to Marker et al. on Nov. 5, 1996, disclose processes that involve distillation by fractionation and membrane separation by vapor permeation in a single vessel. The distillation zone can be positioned upstream or downstream of the membrane separation zone. The process can be used to separate alcohol, e.g. isopropyl alcohol, and water.

U.S. Pat. No. 5,897,750 issued to Berg on Apr. 27, 1999 describes a method that uses extractive distillation for separating acetone, isopropyl alcohol, and water.

U.S. Pat. No. 5,494,556 issued to Mita et al. discloses a method for separating a liquid mixture, such as isopropyl alcohol and water. In the method, the liquid mixture is heated then supplied to a pervaporation membrane module to separate a permeable component of the liquid, a portion of non-permeated liquid is circulated through a circulation pipe into a liquid mixture feeding pipe before a heater, and the remaining portion of the non-permeated liquid is extracted to the outside of the system, and wherein the temperature of the liquid mixture feeding pipe in which the non-permeated liquid has been mixed with the liquid mixture or in the circulation pipe for the non-permeated liquid, is measured, and when the measured temperature is out of a predetermined range, new supply of the liquid mixture and/or extraction of the non-permeated liquid is stopped.

The methods taught in the prior art, do not necessarily meet the requirements of today's customers, such as the semiconductor industry. As such, a process for preparing ultra-high purity isopropyl alcohol is needed to meet the new demands of customers.

The present invention also provides many additional advantages which shall become apparent as described below.

SUMMARY OF THE INVENTION

The present invention is directed to a process for producing high purity isopropyl alcohol. The process comprises the steps of: (a) feeding a feed stream comprising at least about 99.9 wt. % isopropyl alcohol into a separation column; (b) separating the isopropyl alcohol into an overhead stream which is taken overhead from the separation column and a bottoms stream taken as bottoms from the separation column; and (c) removing the high purity isopropyl alcohol at a point: (i) below where the feed stream enters the separation column but above the bottoms stream, or (ii) above where the feed stream enters the separation column but below the overhead stream, wherein the high purity isopropyl alcohol has a metals content of less than about one part per billion (ppb) and a water content of less than about 100 parts per million (ppm). Optionally, the process includes the further step of passing the high purity isopropyl alcohol through an ion exchange resin after removing the high purity isopropyl alcohol from the separation column, thereby forming an ultra-high purity isopropyl alcohol that contains less than 100 parts per trillion (ppt) of any metal impurity.

High purity isopropyl alcohol may also be produced by a process comprising the steps of: (a) feeding a feed stream comprising at least about 99.9 wt. % isopropyl alcohol into a separation column; (b) separating the isopropyl alcohol into an overhead stream which is taken overhead from the separation column and a bottoms stream taken as bottoms from the separation column, wherein the overhead stream comprises the high purity isopropyl alcohol having a metals content of less than about 1 ppb and a water content of less than about 100 ppm. The high purity isopropyl alcohol may further be processed through an ion exchange resin after collecting the high purity isopropyl alcohol from the overhead stream, thereby forming an ultra-high purity isopropyl alcohol that contains less than 100 ppt metal impurities.

Other and further objects, advantages and features of the present invention will be understood by reference to the following specification in conjunction with the annexed drawings wherein like parts have been given like numbers.

DETAILED DESCRIPTION OF THE INVENTION

Figure 1:
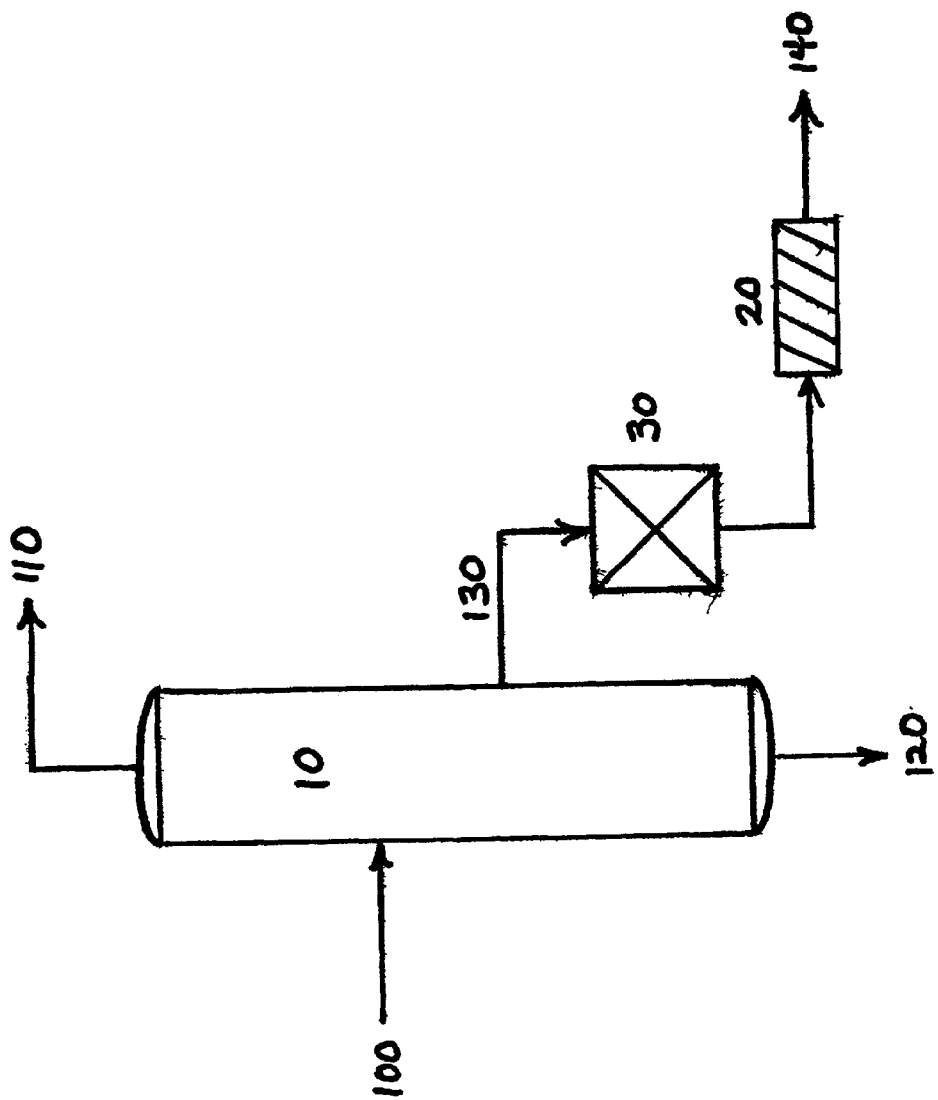
FIG. 1 is a process flow diagram of a first embodiment of the present invention.
Figure 2:
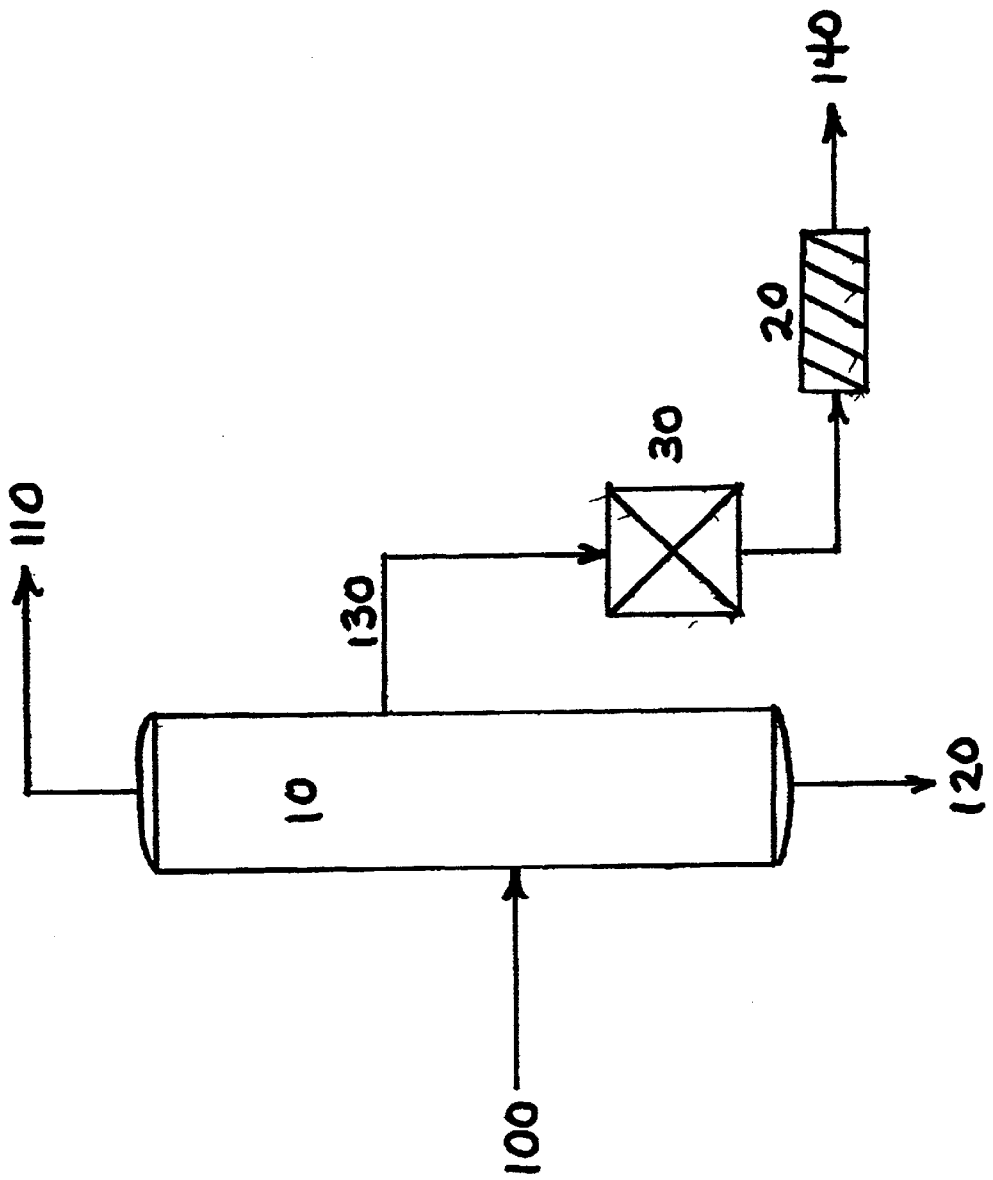
FIG. 2 is a process flow diagram of a second embodiment of the present invention.
Figure 4:
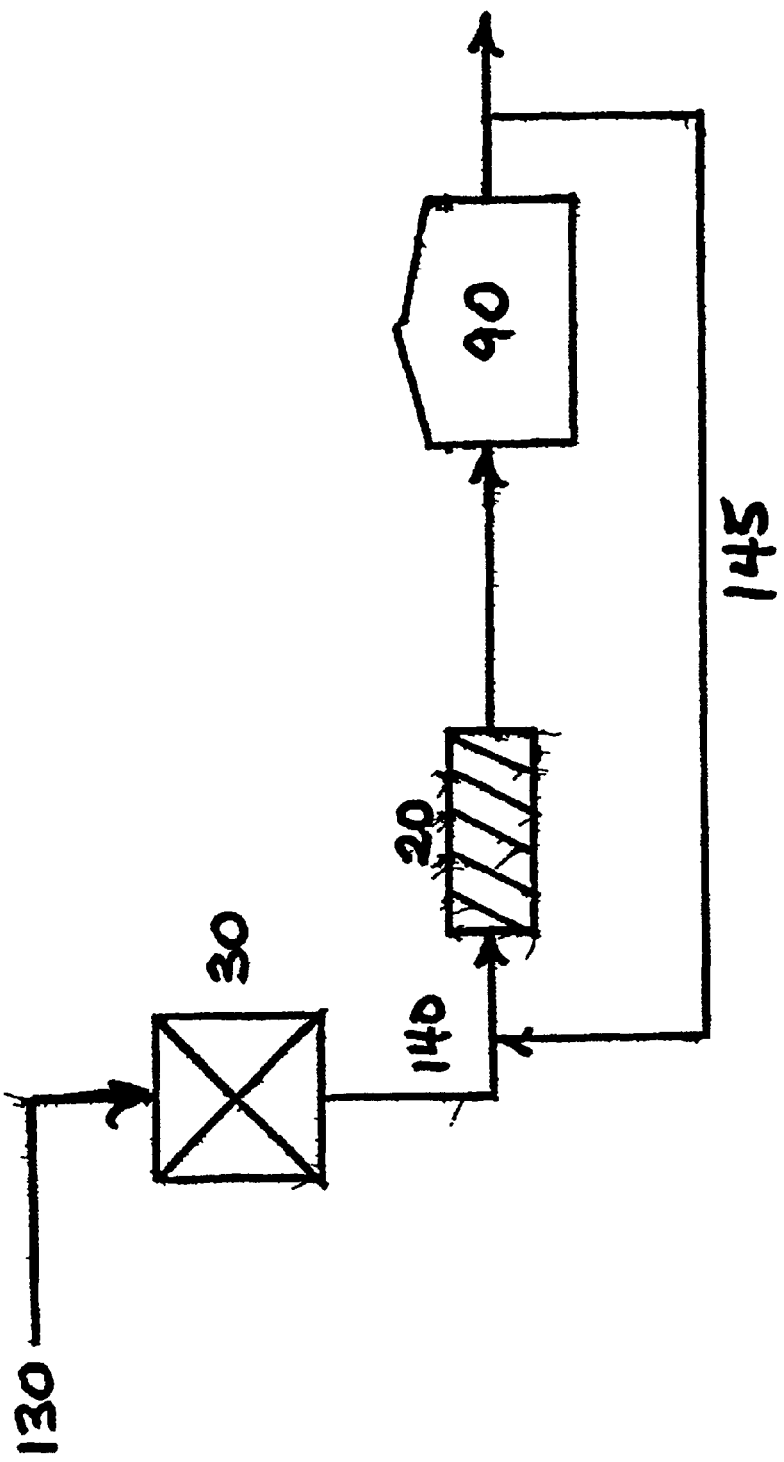
FIG. 4 is a process flow diagram showing the optional steps of ion exchanging, filtering, and recirculating the isopropyl alcohol product.
Figure 5:
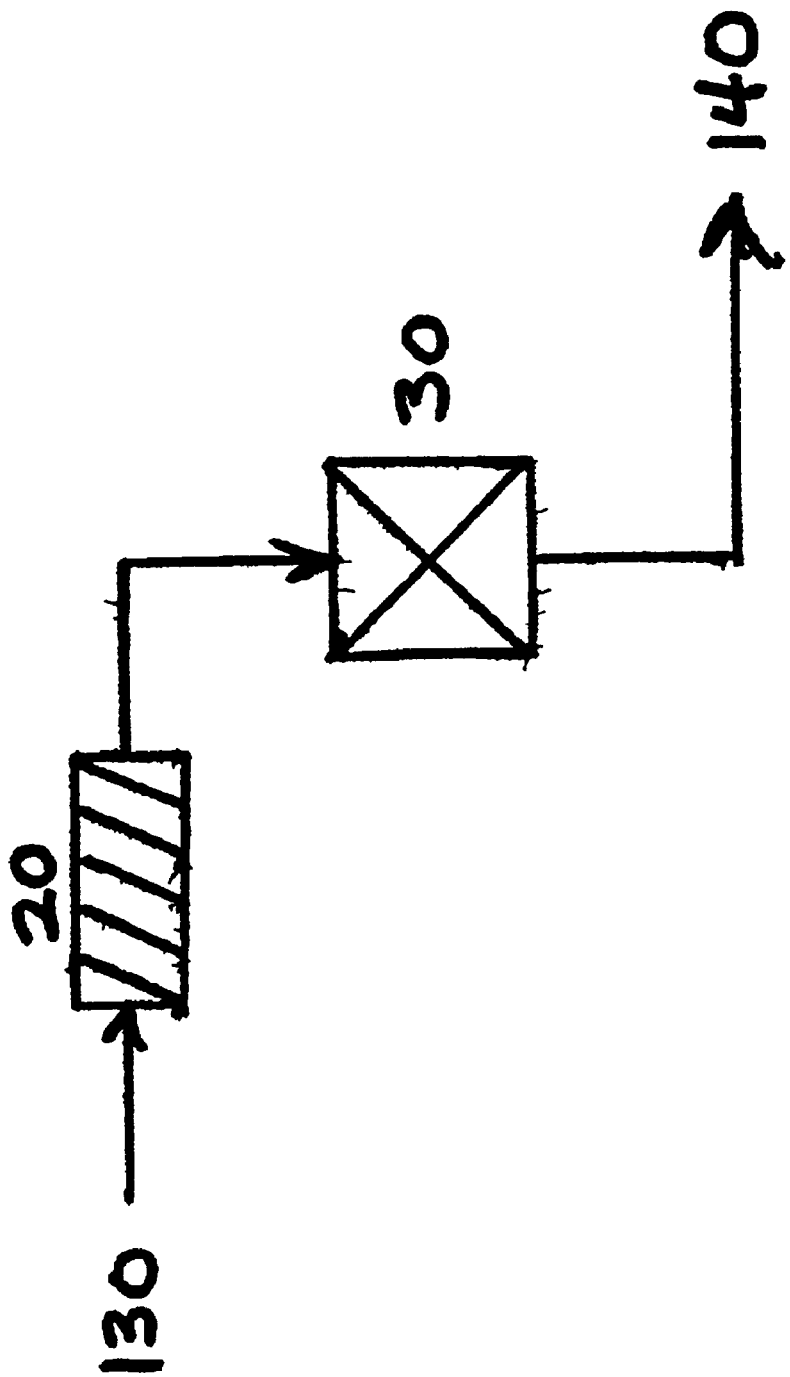
FIG. 5 is a process flow diagram showing the optional steps of ion exchanging and filtering the isopropyl alcohol product.

In FIG. 1, high purity isopropyl alcohol is produced utilizing separation column 10. Dry isopropyl alcohol 100 that is at least about 99.9 wt. % isopropyl alcohol is fed into the separation column. Overhead stream 110 from the separation column is about 5 to 30 wt. % of the isopropyl alcohol and bottoms stream 120 is about 5 to 30 wt. % of the isopropyl alcohol. The high purity isopropyl alcohol is taken as vapor sidestream 130, which has a metals content of less than about 1 ppb and a water content of less than about 100 ppm. This meets the stringent requirements demanded by the Semiconductor Industry. In FIG. 1, the vapor sidestream is taken from the separation column, below the feed entrance point but above the bottoms stream. However, depending on the separation column configuration, the vapor sidestream can be taken from the separation column above the feed entrance point but below the overhead stream, as shown in FIG. 2. In addition, the process shown in FIG. 1, shows the optional steps of passing the high purity isopropyl alcohol through an ion exchange resin 30 then through filtering device 20, such as a membrane. Alternatively, the ion exchange resin can be situated after the filter, as shown in FIG. 5. Once treated with the ion exchange resin, the high purity isopropyl alcohol becomes an ultra-high purity isopropyl alcohol that contains less than about 100 ppt of any metal impurity. In a further embodiment, recirculation line 145 may be included after holding tank 90, which may be a shipping container, to pass the ultra-high purity isopropyl alcohol through the filtering device one or more times, as shown in FIG. 4.

Figure 6:
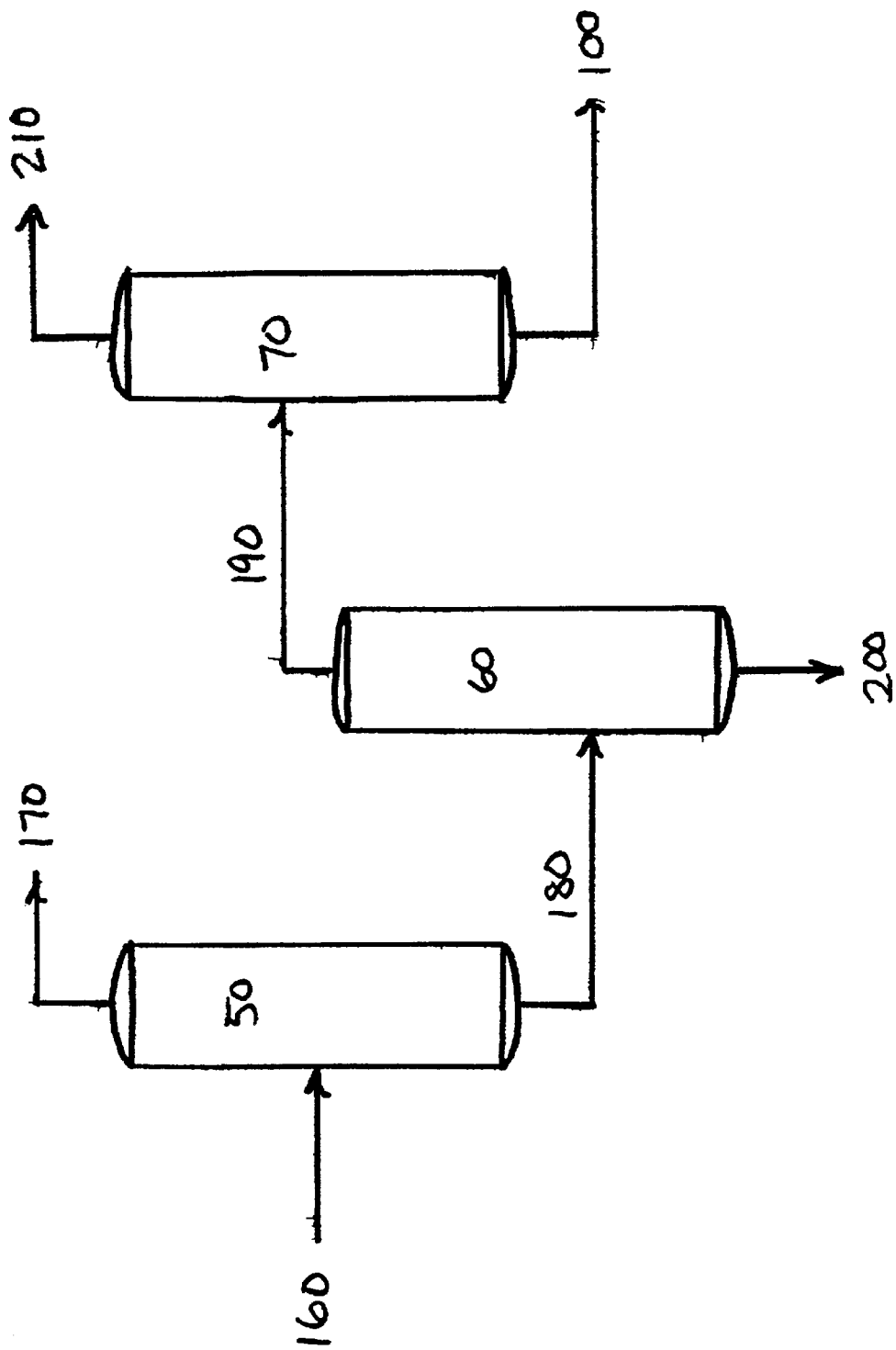
FIG. 6 is a process flow diagram showing a method for making 99.9 wt. % isopropyl alcohol.

The process for producing high purity isopropyl alcohol begins by feeding or providing isopropyl alcohol to a separation column. The isopropyl alcohol is at least 99.9 wt. % isopropyl alcohol, which can be produced by various methods. One such method for producing the at least 99.9 wt. % isopropyl alcohol solution is shown in FIG. 6, where crude isopropyl alcohol 160 may be initially purified by removing light organic substances 170 that have boiling points lower than isopropyl alcohol. This may be performed in a separating unit such as first distillation column 50, where the crude isopropyl alcohol is distilled. The light organic substances are removed as an overhead product using extractive distillation in the first distillation column and partially purified aqueous isopropyl alcohol 180 is taken as the bottom product. The partially purified aqueous isopropyl alcohol is then subjected to another separation treatment in a second separation unit, such as second distillation column 60. The second distillation column separates water and isopropyl alcohol via azeotropic distillation. This produces an aqueous isopropyl alcohol 190, which is taken as overhead product from the second distillation column and further purified in a third separation unit, such as third distillation column 70. The aqueous isopropyl alcohol feed into the third distillation column has a water content of about 14 wt. % or less. The third column removes essentially all the water from the isopropyl alcohol solution by utilizing ternary azeotropic distillation. Ternary azeotropic distillation requires the use of a third component in addition to isopropyl alcohol and water, which is recycled and reused internally in the tower. Water is removed from the isopropyl alcohol solution so that a dry isopropyl alcohol solution 100 is at least about 99.9 wt. % isopropyl alcohol containing 200–500 ppm of organic impurities and having a moisture content of 100 ppm or less. This dry isopropyl alcohol product is suitable for use in the process of the present invention, which is exemplified in FIGS. 1, 2, and 3.

Separation column 10 may be any device that is capable of separating, fractionating, distilling, purifying, or extracting components from a liquid. For example, the separation column can be a distillation column. The separating step is used to remove components with boiling points different from that of isopropyl alcohol. Overhead stream 110 is about 5 to 40 wt. % of the isopropyl alcohol and contains increased concentrations of components having a boiling point less than isopropyl alcohol. Bottoms stream 120 is about 5 to 40 wt. % of the isopropyl alcohol and has increased concentrations of components having a boiling point greater than isopropyl alcohol.

Removing high purity isopropyl alcohol from separation column 10 is performed at a point in the separation process that is determined after careful analysis. Samples may be taken throughout the process. The high purity isopropyl alcohol product is removed at a point where the metals content is 1 ppb and the moisture content is 100 ppm.

In a preferred embodiment, separation column 10 may be a distillation column configured with about 20 to 70 trays. Since isopropyl alcohol feed 100 is at least about 99.9 wt. % isopropyl alcohol, the distillation column is preferably configured with about 30 to 60 trays. Typically, the feed entrance point is located between tray 20 to 50. Depending on the configuration of the distillation column, vapor sidestream 130 is situated above or below the feed entrance point. The location of the vapor sidestream is carefully chosen to ensure that the isopropyl alcohol stream selected is high in purity and quality. That is, the high purity isopropyl alcohol product has a metals content of less than about 1 ppb and a water content of less than, about 100 ppm. Preferably, the vapor sidestream is taken between about tray 20 to tray 50.

Figure 3:
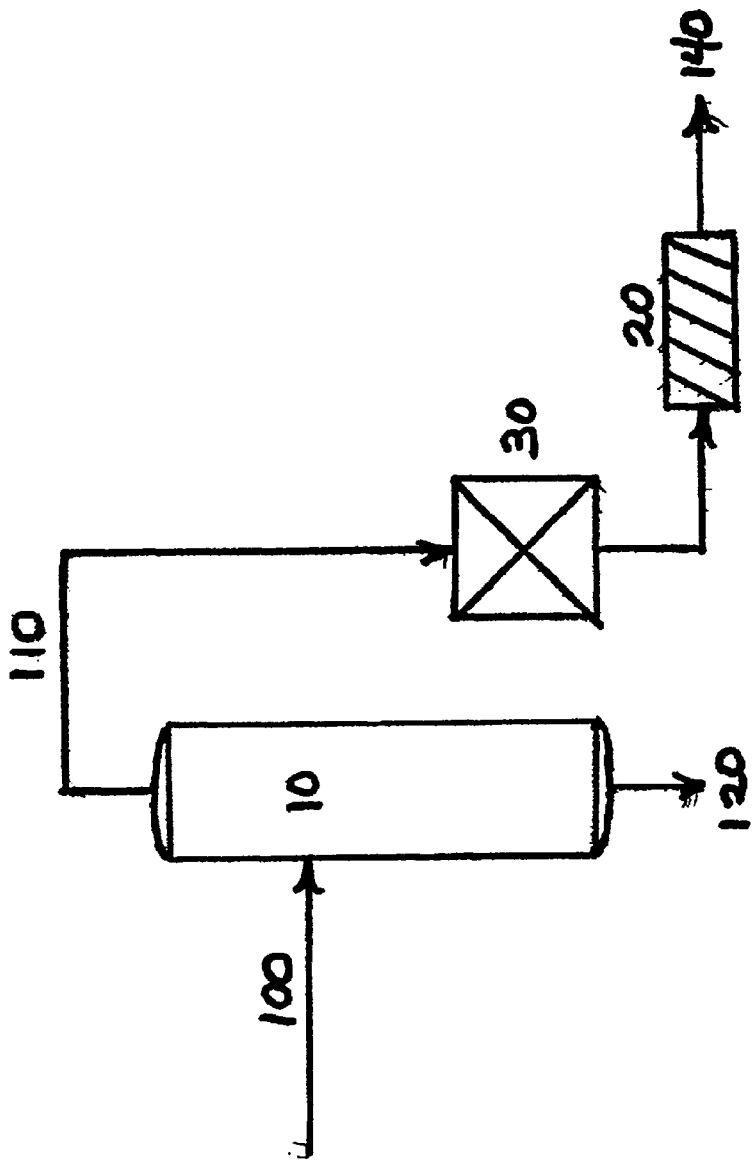
FIG. 3 is a process flow diagram of a third embodiment of the present invention.

In another embodiment, the process for producing high purity isopropyl alcohol is shown in FIG. 3. It begins by feeding a feed stream comprising at least about 99.9 wt. % isopropyl alcohol into a separation column, such as distillation column 10. The at least about 99.9 wt. % isopropyl alcohol is separated into an overhead stream 110, which is taken from the top of the separation column and bottoms stream 120 taken as bottoms from the separation column. The overhead product 110 from the distillation column is collected as the high purity isopropyl alcohol product, which has a metals content of less than about 1 ppb and a water content of less than about 100 ppm. Optionally, the high purity isopropyl alcohol product is filtered by passing the high purity isopropyl alcohol through filtering device 20 to remove particles. The high purity isopropyl alcohol may further be treated with ion exchange resin 30. This results in an ultra-high purity isopropyl alcohol product having less than about 100 ppt of any metal impurity. Here again, the filtering device may be placed after the ion exchange resin as shown in FIG. 3.

The step of separating the isopropyl alcohol solution is performed in any apparatus capable of separating, fractionating, distilling, purifying, or extracting isopropyl alcohol, such as separation column 10. In the embodiment depicted in FIG. 3, overhead stream 110 and bottoms stream 120 are derived from the separating step. The overhead stream is about 60 to 98 wt. % of the weight of feed stream 100 and contains components with a boiling point less than isopropyl alcohol and the bottoms stream is about 2 to 40 wt. % of the feed stream. More preferably, the overhead stream is about 70 to 80 wt. % of the feed stream and the bottoms stream is about 2 to 30 wt. % of the feed stream.

The high purity isopropyl alcohol is collected from the overhead product that exits distillation column 10. At this point, the high purity isopropyl alcohol has a metals content of less than 1 ppb of any metal impurity and a moisture content of less than 100 ppm.

Once high purity isopropyl alcohol is produced, an ion exchange resin can be optionally included for use with any of the methods described in the present invention. As discussed above, the processes shown in FIG. 1 and FIG. 2, are shown with ion exchange resin 30. The ion exchange resin is comprised of a solid phase that contains bound groups that carry a positive or negative ionic charge. Moreover, there are exchangeable counter ions on the resin that can be displaced. By including a step for treating the high purity isopropyl alcohol with an ion exchange resin, an ultra-high purity isopropyl alcohol is obtained, where the ultra-high purity isopropyl alcohol contains less than about 100 ppt of any metal impurity. This additional step further purifies the high purity isopropyl alcohol by removing additional metal impurities and counter ions, e.g. anions and cations.

Ion exchange resin 30 may be any suitable resin capable of removing metal impurities. Metal impurities include all metal ions, such as sodium, potassium, calcium, and iron. Preferably, the ion exchange resin is a cationic resin, an anionic resin, or mixtures thereof. One such resin is available from Rohm and Haas, sold under the tradename AMBERLIGHT UP604 RESIN or AMBERJET UP6040. If an acidic resin is used, cations are removed, which includes most metals. In this case, the ultra-high purity isopropyl alcohol may be subjected to an additional treatment with an anionic resin to further remove anions. The cation metal absorption frees up anion counter ions that can be absorbed by the anion resin. In addition, the anion resin is capable of removing trace acidic compounds from the isopropyl alcohol that can cause cation release. The resins can be chosen on the basis of what species need to be removed. Single resin beds can be used alone or in various combinations. Moreover, the ion exchange resin that is used can be a hybrid device consisting of resin impregnated filters or membranes.

The process may further contain the optional step of passing the high purity isopropyl alcohol or ultra-high purity isopropyl alcohol through filtering device 20. In FIG. 1, the filtering device is situated after the ion exchange resin. The filtering device can be any suitable device capable of removing particles ranging in size from 0.05 microns ($\mu$m) to 10 $\mu$m. Preferably, the filtering device is selected from the group consisting of a membrane, a microfiltration device or cartridge, an ultra-filtration device, or combinations thereof. A membrane is simply a permeable or semi-permeable material through which two or more species can be transported at different rates by applying a driving force across the material. This driving force is typically applied in the form of a pressure or concentration gradient. The different transport rates of various species across the membrane are the result of differences in size, solubility, or diffusivity or combinations thereof. Suitable membranes include, but are not limited to, ceramic membranes, polymeric membranes, metallic membranes, and mixtures thereof. Here again, the high purity isopropyl alcohol produced by the methods of the present invention may be passed through such a filtering device, with the intent to remove all particulates.

The processes previously described may alternatively be configured so that the filtering device is situated before ion exchange resin 30. In this setup, high purity isopropyl alcohol is the product that is passed through the filtering device to remove undesirable particles.

To illustrate the present invention, the following examples are provided. It should be understood that the present invention is not limited to the examples described.

EXAMPLE 1

An isopropyl alcohol stream containing 350 ppt calcium, 136 ppt potassium, and 544 ppt sodium was passed through a 24 inch resin bed of AMBERLITE UP604 at 30 volumes per volume of resin bed per hour. The effluent contained 50 ppt or less of calcium, 50 ppt or less of potassium, and 34 ppt or less of sodium;

EXAMPLE 2

Results of filtration experiments are shown in the table below.

| Particle Size ($\mu$m) | Particle Count per milliter | | | | | | | |
|---|---|---|---|---|---|---|---|---|
| | Filter #1 | | Filter #2 | | Membrane #1 | | Membrane #2 | |
| | Pre-Filter | Post-Filter | Pre-Filter | Post-Filter | Pre-Membrane | Post-Membrane | Pre-Membrane | Post-Membrane |
| ≧0.30 | 1400 | 790 | 4200 | 1200 | 12000 | 200 | 12000 | 1000 |
| ≧0.50 | 290 | 180 | 1300 | 290 | 6400 | 110 | 5500 | 260 |
| ≧0.75 | 52 | 18 | 110 | 25 | 3700 | 69 | 3000 | 62 |
| ≧1.00 | 11 | 2.8 | 10 | 6.7 | 1500 | 37 | 1100 | 19 |
| ≧2.00 | 2.2 | 1 | 1.6 | 1.2 | 43 | 3 | 31 | 2.3 |
| ≧5.00 | 1 | 1 | 1 | 1 | 5.3 | <1 | 2.5 | <1 |

The present invention has been described with particular reference to the preferred forms thereof. It will be obvious to one of ordinary skill in the art that changes and modifications may be made therein without departing from the spirit and scope of the present invention as defined by the following claims.

What is claimed is:

1. A process for producing high purity isopropyl alcohol comprising the steps of:
   (a) feeding a feed stream consisting essentially of at least 99.9 wt % isopropyl alcohol containing 200 to 500 ppm organic impurities and having a moisture content of 100 ppm or less into a separation column;
   (b) separating said feed stream into an overhead stream, containing increased concentrations of components having a boiling point less than isopropyl alcohol, taken overhead from said separation column and a bottoms stream, containing increased concentrations of components having a boiling point greater than isopropyl alcohol, taken as bottoms from said separation column, wherein any isopropyl alcohol in said overhead stream and said bottoms stream is not high purity isopropyl alcohol; and
   (c) removing said high purity isopropyl alcohol as a vapor sidestream at a point:
      (i) below where said feed stream enters said separation column but above said bottoms stream, or
      (ii) above where said feed stream enters said separation column but below said overhead stream,
   wherein said high purity isopropyl alcohol has a metals content of less than about 1 ppb and a water content of less than about 100 ppm.

2. The process of claim 1, further comprising the step of passing said high purity isopropyl alcohol through a filter after removing said high purity isopropyl alcohol from said separation column, wherein said filter is selected from the group consisting of: a membrane, a microfiltration cartridge, an ultra-filtration device, and mixtures thereof.

3. The process of claim 2, wherein said filter is a membrane selected from the group consisting of: ceramic membranes, polymeric membranes, metallic membranes, and mixtures thereof.

4. The process of claim 1 or 2, further comprising the step of passing said high purity isopropyl alcohol through an ion exchange resin, thereby forming an ultra-high purity isopropyl alcohol having less than about 100 ppt of any metal impurity.

5. The process of claim 4, wherein said ion exchange resin is at least one resin selected from the group consisting of: a cationic resin, an anionic resin, and mixtures thereof.

6. The process of claim 4, further comprising the step of passing said ultra-high purity isopropyl alcohol through a filter, wherein said filter is selected from the group consisting of: a membrane, a microfiltration cartridge, an ultra-filtration device, and mixtures thereof.

7. The process of claim 6, wherein said filter is a membrane selected from the group consisting of ceramic membranes, polymeric membranes, metallic membranes, and mixtures thereof.

8. The process of claim 1, wherein said separation column is a distillation column.

9. The process of claim 8, wherein said overhead stream comprises about 5 to 30 wt. % of said feed stream and said bottoms stream comprises about 5 to 30 wt. % of said feed stream.

10. The process of claim 1, wherein said at least 99.9 wt. % isopropyl alcohol is produced by a method comprising the step of distilling an isopropyl alcohol solution that contains no more than about 14 wt. % water using a ternary azeotrope.

* * * * *